United States Patent [19]

Kroeger et al.

[11] Patent Number: 4,464,195

[45] Date of Patent: Aug. 7, 1984

[54] HERBICIDAL AGENTS BASED ON N-(3,4-DICHLOROPHENYL)-N'METHOXY-N'-METHYLUREA AND BENZOTHIADIAZINONE DIOXIDES

[75] Inventors: Ingo Kroeger, Mountain Lakes, N.J.; Bruno Wuerzer, Otterstadt, Fed. Rep. of Germany

[73] Assignee: BASF Aktiengesellschaft, Fed. Rep. of Germany

[21] Appl. No.: 346,095

[22] Filed: Feb. 5, 1982

[51] Int. Cl.³ ............................................. A01N 43/32
[52] U.S. Cl. .......................................... 71/91; 71/120
[58] Field of Search ................................... 71/91, 120

[56] References Cited

U.S. PATENT DOCUMENTS

| | | | |
|---|---|---|---|
| 2,960,534 | 11/1960 | Scherer et al. | 260/553 |
| 3,079,244 | 2/1963 | Scherer et al. | 71/2.6 |
| 3,708,277 | 1/1973 | Zeidler et al. | 71/91 |
| 3,912,489 | 10/1975 | Fischer | 71/91 |
| 4,158,559 | 6/1979 | Stubenrauch et al. | 71/91 |

FOREIGN PATENT DOCUMENTS

2443901  3/1975  Fed. Rep. of Germany.

*Primary Examiner*—Catherine L. Mills
*Attorney, Agent, or Firm*—Keil & Weinkauf

[57] ABSTRACT

Herbicidal agents containing a composition of a 1H-2,1,3-benzothiadiazin-4(3H)-one-2,2-dioxide and N-(3,4-dichlorophenyl)-N'-methoxy-N'-methylurea in a weight ratio of from 1:0.05 to 1:0.2. These agents are particularly suitable for combating unwanted plant growth in soybeans.

1 Claim, No Drawings

HERBICIDAL AGENTS BASED ON N-(3,4-DICHLOROPHENYL)-N'METHOXY-N'-METHYLUREA AND BENZOTHIADIAZINONE DIOXIDES

The present invention relates to herbicidal agents containing compositions of N-(3,4-dichlorophenyl)-N'-methoxy-N'-methylurea and benzothiadiazinone dioxides, and a process for combating the growth of unwanted plants with these herbicidal agents.

The herbicidal action of N-(3,4-dichlorophenyl)-N'-methoxy-N'-methylurea has been disclosed (U.S. Pat. No. 2,960,534 and U.S. Pat. No. 3,079,244). The active ingredient may be used as a selective herbicide both before and after emergence of crop plants and unwanted plants. When crop plants, e.g., soybeans, are too heavily damaged by foliage treatment, use must be made of the directed postemergence application technique.

The excellent herbicidal action of 3-alkyl-1H-2,1,3-benzothiadiazin-4(3H)-one-2,2-dioxides, such as 3-isopropyl-2,1,3-benzothiadiazin-(4)-one-2,2-dioxide (bentazon), has also been disclosed (U.S. Pat. No. 3,708,277). However, there are gaps in the action of the commercial product bentazon at the application rates permitted; it has, for example, little effect on Amaranthaceae, which are problem weeds in large parts of the U.S.A. and other areas of the world. For weed control in soybeans, bentazon may be sprayed onto the leaves of the crop without damage being caused.

U.S. Pat. No. 3,912,489 discloses herbicidal compositions of benzothiadiazinone dioxides and urea derivatives, such as N-(3,4-dichlorophenyl)-N'-methoxy-N'-methylurea. These compositions are intended to combat unwanted plants on postemergence application. It is shown that these compositions, at application rates of from 1.0 to 4.0 kg of active ingredient composition per hectare and a ratio of the components of from 3:1 to 1:3 parts by weight, may be applied to the leaves of cereal species. Soybeans are also mentioned as one of the crops in which these compositions may be used. For phytotoxic reasons, the treatment method employed can only be postemergence to weeds; it can also be assumed from the high proportion of N-(3,4-dichlorphenyl)-N'-methoxy-N'-methylurea in these compositions that the technique of directed postemergence application will inevitably have to be employed to prevent significant damage to the soybean plants.

We have now found that the use of herbicidal agents containing a composition of a substituted 1H-2,1,3-benzothiadiazin-4(3H)-one-2,2-dioxide of the formula

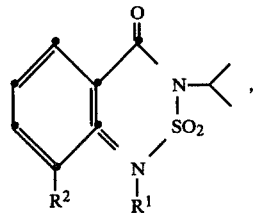

where $R^1$ denotes hydrogen, a cation or cyano, and $R^2$ denotes hydrogen, alkyl of 1 to 4 carbon atoms or halogen, and N-(3,4-dichlorophenyl)-N'-methoxy-N'-methylurea, in a weight ratio of benzothiadiazinone dioxide to urea of from 1:0.05 to 1:0.2, enables weeds to be controlled by applying both components to the foliage of the weeds and soybean plants (overtop application).

Surprisingly, these compositions also have a strong action on Amaranthus spp. and other broadleaved species which do not respond so well to substituted 1H-2,1,3-benzothiadiazin-4(3H)-one-2,2-dioxides.

The agents according to the invention contain, as benzothiadiazine dioxides of the formula I, for example 3-isopropyl-1H-2,1,3-benzothiadiazin-4(3H)-one-2,2-dioxide, 3-isopropyl-8-chloro-1H-2,1,3-benzothiadiazin-4(3H)-one-2,2-dioxide, 3-isopropyl-8-fluoro-1H-2,1,3-benzothiadiazin-4(3H)-one-2,2-dioxide, 3-isopropyl-8-methyl-1H-2,1,3-benzothiadiazin-4(3H)-one-2,2-dioxide and salts of these compounds, suitable salts being substituted or unsubstituted ammonium salts, such as the dimethylammonium and diethylammonium salts, and metal salts, such as alkali metal salts, e.g., the sodium salt; further examples of benzothiadiazinone dioxides of the formula I are 1-cyano-8-chloro-3-isopropyl-2,1,3-benzothiadiazin-4(3H)-one-2,2-dioxide, 1-cyano-8-fluoro-3-isopropyl-2,1,3-benzothiadiazin-4(3H)-one-2,2-dioxide, 1-cyano-8-methyl-3-isopropyl-2,1,3-benzothiadiazin-4(3H)-one-2,2-dioxide, and 1-cyano-3-isopropyl-2,1,3-benzothiadiazin-4(3H)-one-2,2-dioxide (U.S. Pat. No. 3,708,277, German Laid Open Application DE-OS No. 2,443,901, U.S. Pat. No. 4,158,559).

Particularly preferred components of the formula I are 3-isopropyl-1H-2,1,3-benzothiadiazin-4(3H)-one-2,2-dioxide and salts thereof, and 1-cyano-8-chloro-3-isopropyl-2,1,3-benzothiadiazin-4(3H)-one-2,2-dioxide.

The active ingredient ratio to be selected depends first and foremost on the weed spectrum to be combated, the development stage of the weeds and growth conditions. The ratio of benzothiadiazinone dioxide of the formula I to urea varies from 1:0.05 to 1:0.2 parts by weight.

The requisite amount of pure active ingredient composition, i.e. without formulation auxiliaries, also depends on the composition of the stand, the development stage of the plants, and the growth conditions prevailing where the agents are to be applied. Generally, application rates are from 0.25 to 2.0, and preferably 0.5 to 1.5, kg of active ingredient composition per hectare on broadcast application.

The agents according to the invention may be applied postemergence in soybean crops, to the leaves of both crop plants and unwanted plants.

The herbicidal agents according to the invention may also be mixed and applied together with numerous representatives of further herbicidal or growth-regulating active ingredient groups. Compositions particularly effective for extending the spectrum of action in soybean crops are obtained by adding the sodium salt of 2-chloro-4-trifluoromethylphenyl-3'-carboxy-4'-nitrophenyl ether (acifluorphen), 2-[1-(ethoxyimino)-butyl]-5-[2-(ethylthio)-propyl]-3-hydroxy-2-cyclohexen-1-one, or γ-(2,4-dichlorophenoxy)-butyric acid.

It may also be useful to apply the novel agents in admixture with other crop protection agents, e.g., agents for combating pests or phytopathogenic fungi or bacteria. The compounds may also be mixed with mineral salt solutions used to remedy nutritional or trace element deficiencies.

The biological action of the agents according to the invention is demonstrated in the greenhouse experiments and experiments in the open described below.

In the greenhouse experiments, the vessels employed were plastic flowerpots having a volume of 300 cm³ and which were filled with a sandy loam containing about 1.5% humus. The seeds of the test plants were sown shallow, and separately, according to species. Peat was added to the soybean soil to ensure good growth. No impairment of the results need be feared as a consequence of the different soils because the treatment is a postemergence one (leaf application). Plants which had been sown directly in the pots and growth there were used, or plants which had been grown separately as seedlings and transplanted to the experiment vessels a few days before treatment. The test plants had a height, depending on growth shape, of from 3 (e.g., Amaranthus spp.) to 15 cm (e.g., soybean plants). The active ingredients were made up into sprays by suspending or dissolving them in water as vehicle, and applied through finely distributing nozzles. The vessels were set up in a warmer area of the greenhouse (20°–35° C.) to accommodate the heat-loving species. The experiment was run for from 2 to 4 weeks. During this period, the plants were tended and their reactions to the various treatments assessed.

The experiments in the open were run on small plots. The crop plants (soybeans) was sown in rows. The weed flora was natural. The active ingredients were applied in the same formulations as in the greenhouse experiments, individually and as mixtures in water as vehicle, by means of a motor-driven plot spray mounted on a tractor. Treatment was carried out postemergence, i.e., the agents were sprayed onto the leaves of the weeds and crop plants. The observation period extended over several weeks. Assessments were made on a 0 to 100 scale, 0 denoting no damage and 100 complete destruction of at least the visible plant parts.

In the greenhouse experiments and experiments in the open, the following active ingredients were used:
the sodium salt of 3-isopropyl-1H-2,1,3-benzothiadiazin-4(3H)-one-2,2-dioxide (A), and
N-(3,4-dichlorophenyl)-N'-methoxy-N'-methylurea (B).

The greenhouse experiments reveal the non-action or inadequate action of active ingredient A on Amaranthus spp., combined with good soybean tolerance of the 0.25 and 1.0 kg/ha rates, and the comparatively very good herbicidal action of active ingredient B precisely on Amaranthus spp., the crop plant tolerance decreasing as the application rate increases. If the lower rate of 0.25 kg/ha of active ingredient A is mixed with only 0.03 or 0.06 kg/ha of active ingredient B, the combination has a synergistically improved action on Amaranthus spp.

The experiments in the open also reveal the synergistic improvement in the inherently weak action of active ingredient A on Amaranthus spp. as a result of the addition of small amounts of active ingredient B.

TABLE 1

Control of Amaranthus spp. in soybeans; postemergence application in the greenhouse

| Compound | Application Rate kg a.i./ha | Test plants and % damage | |
|---|---|---|---|
| | | Glycine max | Amaranthus spp. |
| A | 0.25 | 0 | 0 |
| | 1.0 | 0 | 30 |
| B | 0.03 | 9 | 80 |
| | 0.06 | 18 | 100 |
| | 0.125 | 27 | 100 |
| A + B | 0.25 + 0.03 | 0 | 100 |

TABLE 2

Postemergence control of Amaranthus spp. in soybeans in the open

| Compound | Application Rate kg a.i./ha | Test plants and % damage | |
|---|---|---|---|
| | | Glycine max | Amaranthus spp. |
| A | 0.5 | 0 | 29 |
| | 1.0 | 0 | 60 |
| B | 0.025 | 3 | 38 |
| | 0.05 | 8 | 78 |
| | 0.1 | 15 | 99 |
| A + B | 0.5 + 0.025 | 3 | 81 |
| | 0.5 + 0.05 | 5 | 89 |

We claim:
1. A process for combating the growth of unwanted Amaranthus spp. plants in soybeans, wherein the leaves of the Aramanthus ssp. plants and soybean plants are treated with a herbicidally effective amount of a herbicidal agent containing a composition of 3-isopropyl-1H-2,1,3-benzothiadiazin-4(3H)-one-2,2-dioxide or a salt thereof and N-(3,4-dichlorophenyl)-N'-methylurea, the weight ratio of benzothiadiazinone dioxide of the formula I to urea being from 1:0.05 to 1:0.2.

* * * * *